United States Patent [19]

DiFilippo

[11] Patent Number: 5,747,812

[45] Date of Patent: May 5, 1998

[54] SCATTER FILTER FOR EMISSION TOMOGRAPHY

[75] Inventor: Frank P. DiFilippo, Mayfield Heights, Ohio

[73] Assignee: Picker International, Inc., Cleveland, Ohio

[21] Appl. No.: 752,588

[22] Filed: Nov. 21, 1996

Related U.S. Application Data

[60] Provisional application No. 60/007,511, Nov. 22, 1995.

[51] Int. Cl.$^6$ .................................................. G01T 1/164
[52] U.S. Cl. ............................... 250/363.1; 378/157
[58] Field of Search ....................... 250/363.03, 363.04; 378/156, 157

[56] References Cited

U.S. PATENT DOCUMENTS

| | | | |
|---|---|---|---|
| 4,563,582 | 1/1986 | Mullani | 250/363.03 |
| 4,618,773 | 10/1986 | Drukier . | |
| 4,857,737 | 8/1989 | Kamae et al. . | |
| 5,524,133 | 6/1996 | Neale et al. | 378/53 |
| 5,602,395 | 2/1997 | Nelleman et al. . | |

FOREIGN PATENT DOCUMENTS 0287707  10/1988  European Pat. Off. .

OTHER PUBLICATIONS

Muehilehner, "Positron Camera with Extended Counting Rate Capability", J. Nucl. Med. (USA), 16 (7), Jul. 1975, pp. 653–657, Jul. 1975.

Primary Examiner—Michael J. Tokar
Assistant Examiner—Richard Hanig
Attorney, Agent, or Firm—Renner, Otto, Boisselle & Sklar, P.L.L.

[57] ABSTRACT

A novel scatter filter for use in positron emission tomography which filters out deflected rays of energy due to Compton scattering which generally have a lower energy. The filter allows most of the undeflected rays to pass through by providing a layer of material having a particular density and atomic number between the detector and the source. Multiple layers of filters may also be provided to filter out characteristic x-rays from the first layer of filter.

19 Claims, 3 Drawing Sheets

SCATTER FILTER FOR EMISSION TOMOGRAPHY

This application claims the benefit of U.S. Provisional Application No. 60/007,511, filed Nov. 22, 1995.

FIELD OF THE INVENTION

The invention described below relates generally to emission tomography, and more particularly, to a scatter filter and method for providing improved emission tomography images.

BACKGROUND OF THE INVENTION

It is often desirable to obtain a visual image of otherwise inaccessible internal areas of a body. Imaging technology used to create such images includes magnetic resonance imaging (MRI), computed tomography (CT), single photon emission computed tomography (SPECT), and positron emission tomography (PET). These technologies have proven particularly useful in the medical field. In PET, for example, a radionuclide is administered internally to a living subject. A positron from the decaying radionuclide encounters and annihilates an electron resulting in a pair of annihilation photons which are emitted in nearly opposite (180°) directions from the annihilation site in the subject.

Scintillation detectors are able to detect the emitted photons (also called gamma rays). When a gamma ray interacts with an atom of a scintillation detector, the gamma ray ejects a single so-called photoelectron or Compton electron. As the ejected electron interacts with the scintillator, it causes the emission of photons in the scintillator, typically in the visible spectrum. The number of photons emitted is proportional to the energy of the ejected electron.

The tomograph is created by recording the location of each flash of visible light and then calculating the location and shape of the source of gamma rays that generated the flashes.

At this point it should be noted that not every gamma ray which hits a scintillation detector will result in a single emitted photoelectron. Some gamma rays will pass through a scintillation detector without any interaction at all. The probability that a gamma ray will interact with a scintillation crystal is a function of the gamma ray's energy, decreasing at higher energy. A graph showing the attenuation ($\alpha$) of gamma rays measured in inverse centimeters ($cm^{-1}$) as a function of energy (E) of the incident gamma ray measured in kiloelectron volts (keV) is included as FIG. 1.

Compton scattering is another factor affecting the resolution and efficiency of both PET and SPECT systems. Compton scattering is a form of direct interaction between an incident photon and an electron in which the electron is ejected from the atom and only a portion of the energy of the photon is absorbed by the electron. The remaining energy of the incident photon is carried by a secondary photon which is scattered incoherently, emerging in a direction that is different from the incident radiation and with reduced energy and a correspondingly longer wavelength.

Compton scattered photons are undesirable in tomography because they degrade the quality of reconstructed images. Compton scattering can and does occur within the body of the subject of the PET or SPECT imaging process. A gamma ray emitted by the radionuclide may travel some distance through the subject's body before undergoing Compton scattering. Because the Compton scattered photons travel in a direction different from the incident photon and from a source remote from the radionuclide, they appear to originate from a different location in the subject's body, and so they distort the reconstructed image. Accordingly, it has been prudent to reject Compton scattered photons before calculating the location and shape of the source of the gamma rays.

Compton scattered photons have been rejected by energy discrimination. Compton scattered photons arrive at the detector with less energy than unscattered gamma rays. During data acquisition, the energy of each incident photon has been measured by the detector. The processing electronics only record events that are within an energy window which is set to the energy range of unscattered gamma rays. Thus the Compton scattered photons which have an energy outside the selected energy window are rejected, with an accuracy limited by the energy resolution of the detector.

In most emission tomography systems, rejecting Compton scattered photons by energy discrimination suffices. However, scatter imposes another limitation in applications where the maximum count rate is approached. Scattered gamma rays trigger the detector, often with a greater probability of interaction than unscattered gamma rays. The scattered events therefore compete with the unscattered events for processing time in the detector, reducing the count rate of the desired unscattered events.

An example of this situation is positron emission tomography on a standard two-head SPECT gamma camera that has been modified for coincidence detection. Such a camera is originally designed for optimal detection of the most commonly used isotope in nuclear medicine, Tc-99m, which emits gamma rays with 140 keV energy. The scintillating crystal is NaI(Tl), ⅜-inch thick. This crystal completely absorbs most 140 keV gamma rays; approximately 90% of the detected counts are in the photopeak. But, the 511 keV gamma rays resulting from positron-emitting isotopes are not absorbed well by the crystal. As shown in FIG. 1, the dominant interaction of the 511 keV gamma rays with the crystal is Compton scattering instead of photoelectric absorption, and the photopeak efficiency of the crystal is about 11%. The situation is worse for coincidence detection of 511 keV gamma rays, since the photopeak efficiency in coincidence is $(11\%)^2$, or about 1%. Thus, in order to achieve a clinically acceptable coincidence count rate (about 5,000 counts per second), the detector must be able to process a very large count rate of individual events (about 500,000 counts per second). Of these 500,000 counts per second, the detector and associated software must reject 495,000 per second as being below the photo peak and therefore the result of Compton scattering and not the result of a gamma ray emitted directly from the radionuclide.

Clearly, Compton scattering is a significant problem in emission tomography. Gamma rays originating within the body have a probability of undergoing Compton scattering before arriving at the detector. In Compton scattering, some of the gamma ray energy is deposited in the body, and the direction of the gamma ray is deflected. In positron emission tomography (PET), this causes an incorrect line of coincidence, and in single photon emission computed tomography (SPECT), this causes an incorrect project count. In both cases, scattered events lead to blurring in the reconstructed images.

SUMMARY OF THE INVENTION

The central idea of the present invention is to prevent scattered events from reaching the detector by placing a "scatter filter" in front of the detector, which primarily absorbs scattered gamma rays while primarily allowing unscattered gamma rays to pass through. The benefits of such a scatter filter are twofold. First, the detector's maximum photopeak count rate is potentially increased. Eliminating primarily scattered photons allows a greater activity of radionuclide to be used before saturating the detector, resulting in an increased photopeak count rate.

Second, using dual energy windows can improve image quality. In addition to the energy window around the photopeak, some nuclear imaging systems employ a second window in the Compton spectrum, under the assumption that Compton scattered photons originating within the subject's body are negligible compared to the Compton-scattered photons originating within the detector. Use of dual energy windows improves the sensitivity of the detector, at the expense of increased scatter fraction. (Scatter fraction is defined as the ratio of scatter events to the total number of events.) With a scatter filter in front of the detector, Compton scattered photons originating in the subject's body comprise a smaller fraction of the photons in the secondary energy window, leading to reduced degradation of image quality.

One aspect of the present invention is a scatter filter for use in a gamma camera used for Positron Emission Tomography of a body, the filter discriminating between primary gamma rays which are emitted by a radionuclide and scattered gamma rays which result from a primary gamma ray being absorbed by a part of the body being imaged and re-radiated at a lower energy, the filter including a first layer of material positioned in front of a detector of a gamma camera and having a relatively low attenuation of primary gamma rays and a relatively high attenuation of scattered gamma rays.

Another aspect of the present invention is the foregoing and including a second layer, the second layer being of a material which has an absorption spectrum to substantially absorb radiation emitted by the first layer as a result of the first layer's absorbing a scattered gamma ray and re-emitting it at a lower energy and the second layer being substantially transparent to primary gamma rays, the second layer being positioned between the first layer and the detector of the gamma camera.

Another aspect of the present invention is a filter for use with an emission tomography camera used to create an image of a body and which has a detector with a surface for detecting gamma rays emitted from the body, the filter discriminating between primary gamma rays of a first, high energy emitted from the body and scattered gamma rays of a second, lower energy, the filter comprising a material having a substantial difference in attenuation at the energy levels of the primary and scattered gamma rays, the filter being formed in a first layer positioned between the body being imaged and the detector covering substantially the entire surface of the detector.

Another aspect of the present invention is the foregoing, further including a second layer, the second layer having an absorption spectrum to substantially absorb radiation emitted by the first layer as a result of the first layer's absorbing a scattered gamma ray and re-emitting it at a lower energy and the second layer being substantially transparent to primary gamma rays, the second layer being positioned between the first layer and the detector of the gamma camera.

Yet another aspect of the present invention is the foregoing, further including a plurality of strips of material positioned between the body being imaged and the first layer of the filter, the strips of material absorbing primary gamma ray which arrive at the detector at selected angles of incidence.

The foregoing and other features of the invention are hereinafter fully described and particularly pointed out in the claims, the following description and the annexed drawings setting forth in detail a certain illustrative embodiment of the invention, this being indicative, however, of but one of the various ways in which the principles of the invention may be employed.

DETAILED DESCRIPTION OF THE INVENTION

Figure 1:
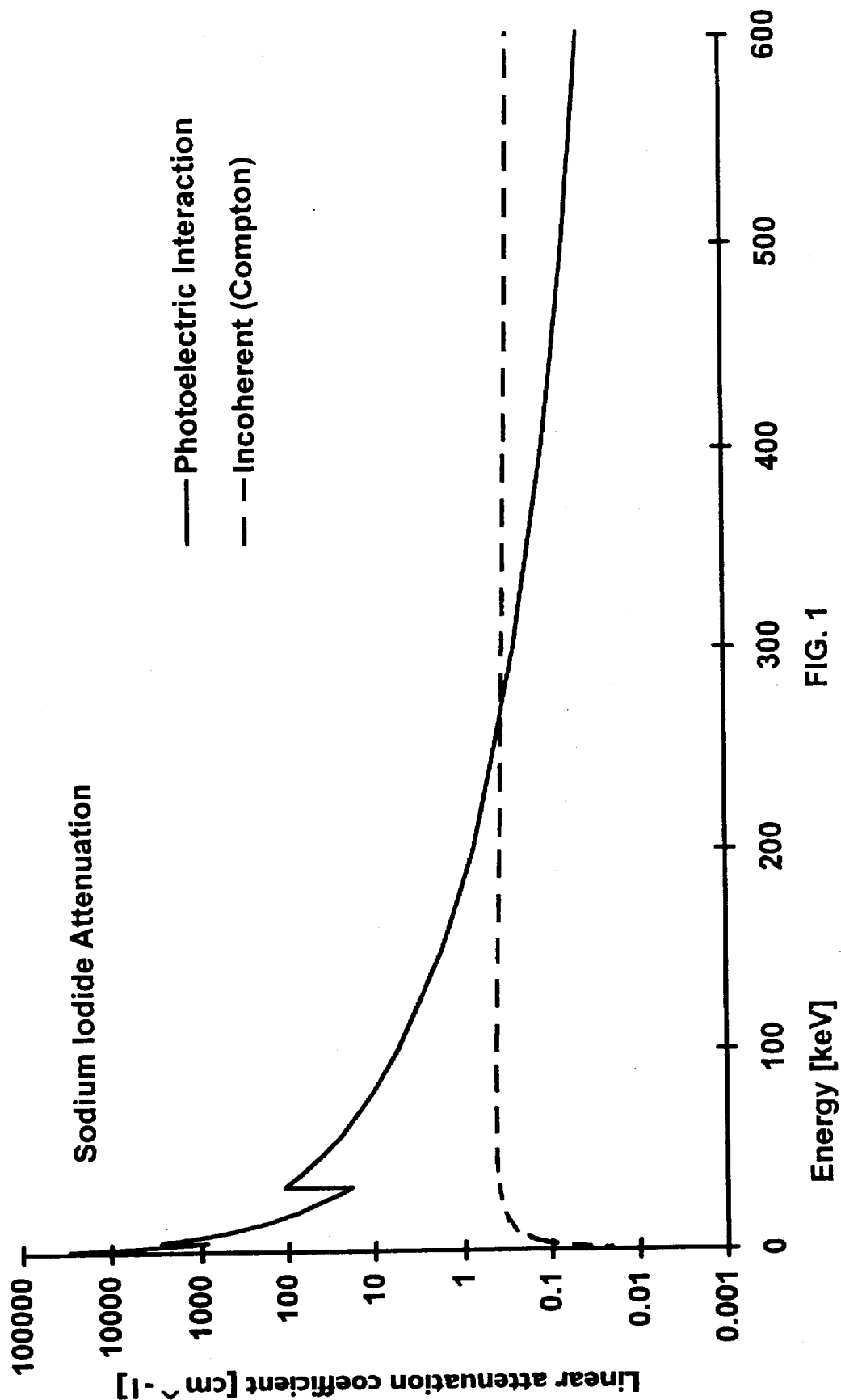
FIG. 1 is a graph showing the attenuation ($\alpha$) of gamma rays measured in inverse centimeters ($cm^{-1}$) as a function of energy (E) of the incident gamma ray measured in kiloelectron volts (keV) for sodium Iodide, a typical scintillator material.
Figure 2:
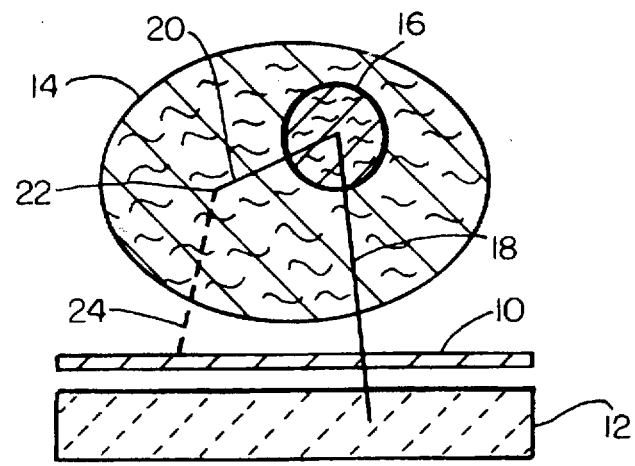
FIG. 2 illustrates the function of a scatter filter according to the present invention.

FIG. 2 shows a scatter filter 10 positioned between a scintillation detector 12 and the body 14 of a subject which contains a source 16 of gamma rays. When a gamma ray is emitted by the source 16 and is not scattered within the body 14, it takes a direct path 18, passing through the filter 10, and reaches the detector 12. Such a gamma ray has an energy $E_0$ characteristic of the source 16. When a gamma ray 20 is emitted by the source 16 and is scattered as at 22 so as to take a new path 24 (and with necessarily a lower energy), the filter 10 absorbs the gamma ray and the detector 12 is not triggered.

Figure 4:
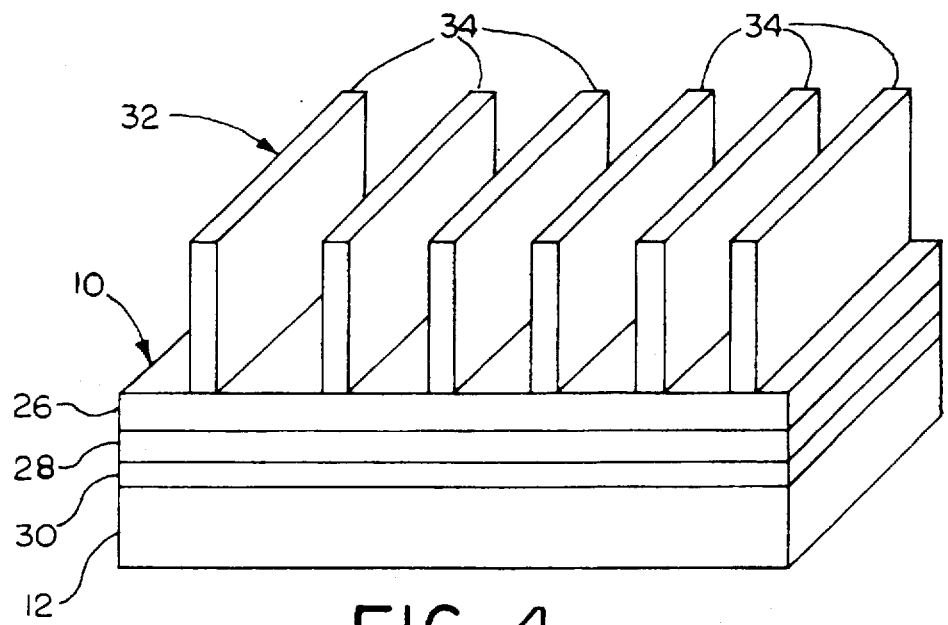
FIG. 4 illustrates one embodiment of the scatter filter constructed in accordance with the present invention.
Figure 3:
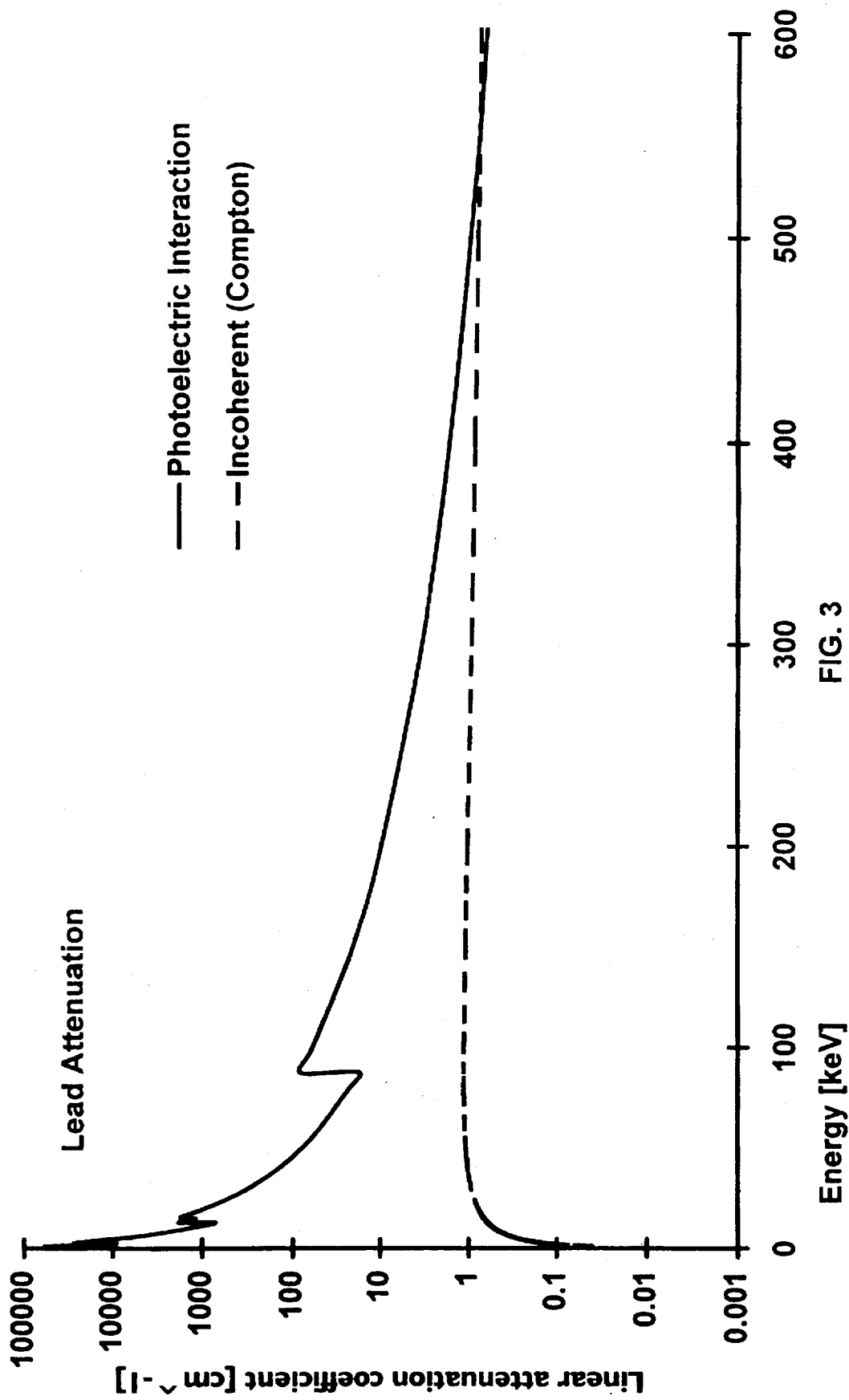
FIG. 3 is a graph showing the attenuation ($\alpha$) of gamma rays measured in inverse centimeters ($cm^{-1}$) as a function of energy (E) of the incident gamma ray measured in kiloelectron volts (keV) for lead.

Scattered photons can have energies spanning the entire spectrum below the photopeak energy $E_0$. Ideally, the scatter filter 10 should have a sharp drop in the attenuation coefficient $\alpha$ just below $E_0$ so that all scattered events are eliminated. However, as a practical matter the variation in $\alpha$ is gradual, and considerable thought must be placed in designing a scatter filter. See FIG. 3. When gamma rays pass through matter, the dominant interaction at low energies is photoelectric absorption, with Compton scattering becoming dominant at higher energies. The energy at which the transition occurs depends on the atomic number Z and density p of the material and is higher for increasing Z and p. The slope of $\alpha$ vs E is also steeper for materials with high Z and p, since photoelectric absorption dominates, and since the attenuation coefficient is most strongly varying in materials with high Z and high p. Another advantage of using a material with a high Z and high p is that a thinner sheet of material is needed to stop the scattered gamma rays. Lead is the most cost-effective choice for a high Z, high p material for discriminating between primary gamma rays with an energy of about 511 keV and a scattered gamma ray energy of about 200 keV. FIG. 4 shows the detector 10 which includes a sheet of lead 26. When the present invention is used to discriminate between other energy differences, other materials may be selected, provided that the attenuation coefficient of the material for the energies to be distinguished is sufficiently different to provide useful results.

Unfortunately, simply placing a sheet of lead 26 in front of the detector 12 is not sufficient. When gamma rays are absorbed in lead, x-rays are often produced, with energies around 80 keV. Many of these x-rays escape the lead and reach the detector, causing the same problems as the scattered gamma rays 24. To absorb these x-rays with minimal interference with the unscattered gamma rays 18, a thin sheet 28 of material of moderate Z and p is placed between the lead 26 and the detector 12. A logical choice for this secondary shield is tin, which absorbs lead x-rays strongly, has a much lower attenuation coefficient at higher energies compared to lead, and is inexpensive. Tin also emits an x-ray at a lower energy (29 keV) which are unlikely to penetrate the detector cover and reach the scintillator. If too many tin x-rays reach the scintillator, an extra layer 30 of lower Z material, such as copper, may be used to attenuate them before reaching the detector 12.

For an exemplary scatter filter to be used on a standard gamma camera for PET imaging (511 keV), a 0.4 mm sheet 26 (FIG. 4) of lead is placed on top of a 0.8 mm sheet 28 of tin. The entire assembly is mounted in front of the detector 12. This scatter filter has a net attenuation of 12% for the unscattered gamma rays at 511 keV. The attenuation is stronger for the scattered gamma rays at lower energies. At 200 keV, the attenuation is 48%, and at 100 keV, the attenuation is about 95%. The x-rays which escape the lead layer 26 are attenuated by more than 50% by the second layer 28 of tin. This configuration greatly reduces the number of scattered gamma rays reaching the detector 12 without a great loss in sensitivity at 511 keV. If a greater sensitivity loss can be tolerated, a thicker sheet of lead could be employed to further reduce the number of scattered events.

The filter of the present invention may also be used in conjunction with what may be termed an "angular filter" 32. This filter consists of a number of rows 34 of lead strips set on edge as shown in FIG. 4. There, the gamma rays which arrive at too oblique an angle to the detector are absorbed by the lead strips. Oblique angle events are less desirable because they degrade the spatial resolution of PET and require the use of more complex reconstruction algorithms. Restricting the angular range of the events also reduces the scatter fraction. Any scattered or secondary emissions from the lead strips 34 are at an energy which is strongly absorbed by the scatter filter 10 between the strips and the detector 12. The spacing of the strips 34 and their height determine the angular window through which gamma rays will be admitted to the scatter filter 10 and the detector 12.

Although the invention has been shown and described with respect to an exemplary embodiment thereof, it is obvious that equivalent alterations and modifications will occur to others skilled in the art upon the reading and understanding of the specification. The present invention includes all such equivalent alterations and modifications, and is limited only by the scope of the following claims.

What is claimed is:

1. A gamma camera used for positron emission tomography of a body, the camera having a detector, which includes a relatively large scintillation crystal, and a scatter filter, the filter discriminating between primary gamma rays which are emitted by a radionuclide and scattered gamma rays which result from a primary ray being absorbed by a part of the body being absorbed by a part of the body being imaged and re-radiated at a lower energy, the filter including:

a first layer of a first material positioned in front of a detector of a gamma camera and having a relatively low attenuation of primary gamma rays and a relatively high attenuation of scattered gamma rays, and a plurality of strips of the first material positioned between the body being imaged and the first layer of the filter, the strips of material absorbing primary gamma rays which arrive at the detector at selected angles of incidence.

2. The camera of claim 1, further including a second layer of material, the second layer having an absorption spectrum to substantially absorb radiation emitted by the first layer as a result of the first layer's absorbing a scattered gamma ray and re-emitting it at a lower energy and the second layer being substantially transparent to primary gamma rays, the second layer being positioned between the first layer and the detector.

3. An emission tomography camera used to create an image of a body and which has a filter and a detector with a relatively large scintillation crystal for detecting gamma rays emitted from the body, the filter discriminating between primary gamma rays of a first, high energy emitted from the body and scattered gamma rays of a second, lower energy, the filter comprising:

a first material having a substantial difference in attenuation at the energy levels of the primary and scattered gamma rays, the filter being formed in a first layer positioned between the body being imaged and the detector covering substantially the entire surface of the detector, and a plurality of strips of the first material positioned between the body being imaged and the first layer of the filter, the strips of material absorbing primary gamma rays which arrive at the detector at selected angles of incidence.

4. The camera of claim 3, further including a second layer of material, the second layer having an absorption spectrum to substantially absorb radiation emitted by the first layer as a result of the first layers' absorbing a scattered gamma ray and re-emitting it at a lower energy and the second layer being substantially transparent to primary gamma rays, the second layer being positioned between the first layer and the detector.

5. A camera as claimed in claim 3, wherein the first material of the filter is selected from the group of materials which substantially block gamma rays having an energy level of approximately 511 keV or less.

6. A camera as claimed in claim 5, wherein the first material of the filter is formed primarily of lead.

7. A camera as claimed in claim 6, wherein the first material of the filter has a thickness of approximately 0.4 mm.

8. A camera as claimed in claim 3, wherein the filter includes a second material positioned between the first material and the detector, the second material blocking radiation emitted by the first material and substantially passing the primary gamma rays to the detector.

9. A camera as claimed in claim 8, wherein the second material of the filter is selected from the group of materials which can substantially block x-rays having an energy level of approximately 80 keV.

10. A camera as claimed in claim 9, wherein the second material of the filter is formed substantially of tin.

11. A camera as claimed in claim 10, wherein the second material of the filter has a thickness of approximately 0.8 mm.

12. A camera as claimed in claim 8, further comprising:

a filter having an additional material positioned between the filter and the detector, the additional material blocking radiation emitted by the second material and substantially passing the primary gamma rays to the detector.

13. A camera as claimed in claim 12, wherein the additional material is selected from the group of materials which can substantially block x-rays having an energy level of approximately 29 keV.

14. A camera as claimed in claim 13, wherein the additional material is formed substantially of copper.

15. An emission tomography camera used to create an image of an object, the camera having a filter and a detector with a relatively large scintillation crystal for detecting gamma rays emitted from the object, the filter comprising:

an outer material covering a substantial portion of the receiving surface area of the detector, said outer material passing primary gamma rays of a first, high energy emitted from the object to the detector and blocking attenuated gamma rays of a second, lower energy from reaching the detector, said outer material having a substantial difference in attenuation at the energy levels of the primary and attenuated gamma rays, wherein the filter is positioned between the object being imaged and the detector, and an angular filter for filtering and collimating incident gamma rays by absorbing attenuated gamma rays approaching the surface of the detector at selected angles, said angular filter including strips extending away from the surface of the outer material and extending away from the detector.

16. An emission tomography camera used to create an image of a body and which has a filter and a detector with a relatively large scintillation crystal for detecting gamma rays emitted from the body, the filter discriminating between primary gamma rays of a first, high energy emitted from the body and scattered gamma rays of a second, lower energy, the filter comprising:

a first material having a substantial difference in attenuation at the energy levels of the primary and scattered gamma rays, the filter being formed in a first layer positioned between the body being imaged and the detector covering substantially the entire surface of the detector, and a plurality of strips of strip material positioned between the body being imaged and the first layer of the filter having a relatively low attenuation of primary gamma rays and a relatively high attenuation of scattered gamma rays, the strips of strip material absorbing primary gamma rays which arrive at the detector at selected angles of incidence.

17. A camera as claimed in claim 16, wherein the first material of the filter and the strip material of the strips are selected from a group of materials which substantially block gamma rays having an energy level of approximately 511 keV or less.

18. A camera as claimed in claim 17, wherein the first material of the filter and the strip material of the strips are formed primarily of lead.

19. A camera as claimed in claim 18, wherein the first material of the filter has a thickness of approximately 0.4 mm.

* * * * *